US012558310B2

(12) United States Patent
Shah et al.

(10) Patent No.: US 12,558,310 B2
(45) Date of Patent: *Feb. 24, 2026

(54) DOSAGE FORM WITH SUSTAINED RELEASE MELATONIN PELLETS

(71) Applicant: SOCIETE DES PRODUITS NESTLE S.A., Vevey (CH)

(72) Inventors: Syed M. Shah, Boca Raton, FL (US); Daniel Hassan, Boca Raton, FL (US)

(73) Assignee: Societe des Produits Nestle S.A., Vevey (CH)

( * ) Notice: Subject to any disclaimer, the term of this patent is extended or adjusted under 35 U.S.C. 154(b) by 743 days.

This patent is subject to a terminal disclaimer.

(21) Appl. No.: 17/758,811

(22) PCT Filed: Jan. 15, 2021

(86) PCT No.: PCT/EP2021/050770
§ 371 (c)(1),
(2) Date: Jul. 14, 2022

(87) PCT Pub. No.: WO2021/144403

PCT Pub. Date: Jul. 22, 2021

(65) Prior Publication Data

US 2023/0045118 A1     Feb. 9, 2023

Related U.S. Application Data

(60) Provisional application No. 62/962,574, filed on Jan. 17, 2020.

(51) Int. Cl.
| | |
|---|---|
| *A61K 9/00* | (2006.01) |
| *A61K 9/20* | (2006.01) |
| *A61K 9/48* | (2006.01) |
| *A61K 9/50* | (2006.01) |
| *A61K 31/4045* | (2006.01) |

(52) U.S. Cl.
CPC .......... *A61K 9/0053* (2013.01); *A61K 9/0056* (2013.01); *A61K 9/0095* (2013.01); *A61K 9/2054* (2013.01); *A61K 9/48* (2013.01); *A61K 9/5047* (2013.01); *A61K 9/5078* (2013.01); *A61K 31/4045* (2013.01)

(58) Field of Classification Search
None
See application file for complete search history.

(56) References Cited

U.S. PATENT DOCUMENTS

| | | | |
|---|---|---|---|
| 8,691,275 B2 | 4/2014 | Shah et al. | |
| 2008/0171085 A1* | 7/2008 | Elnekave | A61K 36/8962 |
| | | | 424/754 |
| 2011/0313055 A1 | 12/2011 | Ervin et al. | |
| 2012/0315337 A1 | 12/2012 | Shah et al. | |
| 2014/0308357 A1* | 10/2014 | Maggi | A61K 9/08 |
| | | | 514/415 |

FOREIGN PATENT DOCUMENTS

| | | | | |
|---|---|---|---|---|
| EP | 3530289 A1 | 8/2019 | | |
| KR | 20040026374 | 3/2004 | | |
| KR | 20040026374 A | * 3/2004 | | A61K 9/16 |
| WO | 9503043 | 2/1995 | | |

OTHER PUBLICATIONS

Kollicoat ® MAE "Resistance", The Chemical Company, Pharma Solutions, pp. 1-14.
"Methocel Cellulose Ethers Technical Handbook", 1997, pp. 1-32.
"Cellets®—Microcrystalline Cellulose Pellets", Pharmaceutical Technology, Jul. 7, 2007, pp. 1-3.
Werner, "Sugar Spheres: a Versatile Excipient for Oral Pellet Medications with modified Release Kinetics", Pharmaceutical Technology Europe, 2006, pp. 35-41.

* cited by examiner

*Primary Examiner* — Lakshmi S Channavajjala
(74) *Attorney, Agent, or Firm* — K&L Gates LLP

(57) ABSTRACT

A composition comprises a therapeutically effective oral pharmaceutical dosage form. The dosage form includes an aqueous carrier material having an acidic pH and a plurality of individual pellets having a first dose of melatonin therein. The individual pellets comprises (i) a solid core; (ii) an active coating over the solid core, the active coating including melatonin and a hydrophilic binder; and (iii) an enteric coating over the active coating. A dissolution pH of the enteric coating is higher than the acidic pH of the aqueous carrier material.

17 Claims, No Drawings

DOSAGE FORM WITH SUSTAINED RELEASE MELATONIN PELLETS

CROSS-REFERENCE TO RELATED APPLICATIONS

The present application is a National Stage of International Application No. PCT/EP2021/050770, filed on Jan. 15, 2021, which claims priority to U.S. Provisional Patent Application No. 62/962,574, filed on Jan. 17, 2020, the entire contents of which are being incorporated herein by reference.

FIELD

This relates to the field of melatonin compositions and, more particularly, to sustained release melatonin dosage forms.

BACKGROUND

Melatonin is a hormone that has been shown to be effective at treating circadian rhythm disorders, sleep disorders, jet lag, shift work syndrome, seasonal affective disease, insomnia, melatonin deficiency in the elderly, and many other conditions. It is typically administered in an oral tablet or liquid drop dosage form.

BRIEF SUMMARY

What is needed is a new melatonin composition that can deliver a sustained release dose of melatonin in dosage form that is easier to swallow than a pill.

An example of such a composition includes a therapeutically effective oral pharmaceutical dosage form including an aqueous carrier material having an acidic pH and a plurality of individual pellets having a first dose of melatonin therein. The individual pellets include a solid core and an active coating over the solid core. The active coating includes melatonin and a hydrophilic binder. An enteric coating is over the active coating. A dissolution pH of the enteric coating is higher than the acidic pH of the aqueous carrier material.

The composition may further include one or more of the following additional features.

The melatonin may be a powder having a median melatonin particle size of 5 μm to 40 μm.

The aqueous carrier material may include a second dose of melatonin therein and dosage form releases the second dose of melatonin into the subject's oral cavity and stomach.

The dosage form is a beverage and the aqueous carrier material includes water.

The dosage form may be a gummy and the aqueous carrier material may be a gummy gelling agent.

The individual pellets may further include a separation coating over the active coating, a subcoat between over the separation coating, and enteric coating over the subcoat. The subcoat may include a hydrogel-forming polymer and an acid, the acid imparting a pH of 0.1 to 4.4 to the hydrogel-forming polymer. The separation coating may separate the acid from the melatonin.

The aqueous carrier material may be hydroxypropyl methylcellulose. The solid core may be a microcrystalline cellulose bead having a diameter of 0.1 to 2 mm. The hydrophilic binder may include hydroxypropyl methylcellulose. The melatonin may be a powder having a median melatonin particle size of 5 μm to 40 μm lodged in the hydrophilic binder. The separation coating may include hydroxypropyl methylcellulose, the hydrogel-forming polymer may include hydroxypropyl methylcellulose, the acid may include citric acid. The separation coating may include hydroxypropyl methylcellulose.

The composition may include any combination of these features.

An example of a treatment method includes administering a therapeutically effective amount of an oral pharmaceutical dosage form to a patient in need thereof. The dosage form includes an aqueous carrier material having an acidic pH and a plurality of individual pellets having a first dose of melatonin therein. The individual pellets include a solid core and an active coating over the solid core. The active coating includes melatonin and a hydrophilic binder. An enteric coating is over the active coating. A dissolution pH of the enteric coating is higher than the acidic pH of the aqueous carrier material.

The method may further include one or more of the following additional features.

The melatonin may be a powder having a median melatonin particle size of 5 μm to 40 μm.

The aqueous carrier material may include a second dose of melatonin therein and dosage form releases the second dose of melatonin into the subject's oral cavity and stomach.

The dosage form may be a beverage and the aqueous carrier material includes water.

The dosage form may be a gummy and the aqueous carrier material may be a gummy gelling agent.

The individual pellets may further include a separation coating over the active coating, a subcoat between over the separation coating, and enteric coating over the subcoat. The subcoat may include a hydrogel-forming polymer and an acid, the acid imparting a pH of 0.1 to 4.4 to the hydrogel-forming polymer. The separation coating may separate the acid from the melatonin.

The aqueous carrier material may be hydroxypropyl methylcellulose. The solid core may be a microcrystalline cellulose bead having a diameter of 0.1 to 2 mm. The hydrophilic binder may include hydroxypropyl methylcellulose. The melatonin may be a powder having a median melatonin particle size of 5 μm to 40 μm lodged in the hydrophilic binder. The separation coating may include hydroxypropyl methylcellulose, the hydrogel-forming polymer may include hydroxypropyl methylcellulose, the acid may include citric acid. The separation coating may include hydroxypropyl methylcellulose.

The dosage form may be therapeutically effective for assisting the patient sleep.

The treatment method may include any combination of these features.

An example of a processing method includes combining an aqueous carrier material with a plurality of individual pellets to form a therapeutically effective oral pharmaceutical dosage form. The aqueous carrier material has an acidic pH. The plurality of individual pellets have a first dose of melatonin therein. The individual pellets include a solid core and an active coating over the solid core. The active coating includes melatonin and a hydrophilic binder. An enteric coating is over the active coating. A dissolution pH of the enteric coating is higher than the acidic pH of the aqueous carrier material.

The method may further include one or more of the following additional features.

The melatonin may be a powder having a median melatonin particle size of 5 μm to 40 μm.

US 12,558,310 B2

3

The aqueous carrier material may include a second dose of melatonin therein and dosage form releases the second dose of melatonin into the subject's oral cavity and stomach.

The dosage form may be a beverage and the aqueous carrier material includes water.

The dosage form may be a gummy and the aqueous carrier material may be a gummy gelling agent.

The individual pellets may further include a separation coating over the active coating, a subcoat between over the separation coating, and enteric coating over the subcoat. The subcoat may include a hydrogel-forming polymer and an acid, the acid imparting a pH of 0.1 to 4.4 to the hydrogel-forming polymer. The separation coating may separate the acid from the melatonin.

The aqueous carrier material may be hydroxypropyl methylcellulose. The solid core may be a microcrystalline cellulose bead having a diameter of 0.1 to 2 mm. The hydrophilic binder may include hydroxypropyl methylcellulose. The melatonin may be a powder having a median melatonin particle size of 5 μm to 40 μm lodged in the hydrophilic binder. The separation coating may include hydroxypropyl methylcellulose, the hydrogel-forming polymer may include hydroxypropyl methylcellulose, the acid may include citric acid. The separation coating may include hydroxypropyl methylcellulose.

The dosage form may be therapeutically effective for assisting the patient sleep.

The method may include any combination of these features.

The processing method may include any combination of these features.

DETAILED DESCRIPTION OF EXAMPLE EMBODIMENTS

A first example of the melatonin composition described here is designed to release melatonin into a subject's gastrointestinal tract in at least one phase that is delivered to the intestines. The composition provides a sustained release of melatonin in the subject's intestines for several hours in order to help the subject remain asleep through the night.

A second example of the melatonin composition described here is designed to release melatonin into a subject's gastrointestinal tract in at least two phases. In a first phase, the composition releases some of its melatonin into the oral cavity and stomach to provide an initial burst dose of melatonin that will help the subject fall asleep. In a second phase, the composition provides a sustained release dose of melatonin in the subject's intestines for several hours in order to help the subject remain asleep through the night.

In these examples, the melatonin is carried by a plurality of individual pellets dispersed in an aqueous carrier material. The aqueous carrier material makes the pellets easy to swallow.

The individual pellets are, at least in part, composed of a solid core and an active coating over the solid core. The active coating includes melatonin from a powder having a median melatonin particle size of 5 μm to 40 μm and lodged in a hydrophilic binder. An enteric coating is over the active coating. The dissolution pH of the enteric coating is higher than the acidic pH of the aqueous carrier material in order to substantially prevent the pellets from releasing melatonin into the aqueous carrier material.

The pellets are individual monolithic bodies that behave like individual small pills in the gastrointestinal tract. Each pellet is composed of its own dose of melatonin and is individually enteric coated. In general, the individual pellets include, but are not limited to a solid core, an active coating, and an enteric coating. Additional details of pellet examples are now provided.

The solid core may be an inert solid material. The inert solid material forms a solid mechanical base or frame over which one or more functional and/or nonfunctional coatings are applied.

One possible example of the inert solid material is a non-pareil sugar bead. A non-pareil sugar bead, sometimes called a sugar sphere, is a pharmaceutical excipient primarily composed of one or more sugars such as sucrose, lactose, D-mannitol, saccharose and the like. The sugar is pharmaceutically inert and digestible by most humans and animals. Some non-pareil sugar beads may include one or more auxiliary components such as corn starch and the like that are also inert and digestible.

Another possible example of the inert solid material is an inert excipient bead. Certain cellulosic materials are acceptable pharmaceutical excipients that can form a solid core with mechanical properties similar to a non-pareil bead. By way of example, microcrystalline cellulose (MCC) pellets or hydroxypropyl methylcellulose (HMPC or hypromellose) are inert and substantially insoluble in water. Because some cellulosic materials such as MCC are insoluble in water, they do not dissolve upon water intrusion as many non-pareil sugar beads would. Accordingly a cellulosic material such as microcrystalline cellulose may be useful when a longer sustained release of melatonin is preferred. Because microcrystalline cellulose is substantially insoluble in water, when the bead remains intact, this may prevent a pellets from immediately dumping their respective doses of melatonin as quickly as they might if the solid core material were soluble.

The shape of the solid core is not limited to any particular shape. Most examples of the solid core may be spheroidal in shape, but other shapes are possible, including amorphous shapes. Spheroidal solid cores of various materials that may be used as inert pharmaceutical carriers are commercially available.

The solid core has a critical dimension, which is the largest measurement from one side of the solid core to the opposite side. For spheroidal cores, the critical dimension is the diameter.

In certain examples of the solid core, the average critical dimension of the solid core is ≤2 mm, 0.1 mm to 2 mm, 0.1 mm to 1.5 mm, 0.1 mm to 1 mm, 0.4 mm to 0.1.5 mm, 0.4 mm to 1.2 mm, 0.4 mm to 0.6 mm, or about 0.5 mm. The critical dimension measurement may be based on mesh size and/or measurements from a particle size analyzer.

The size of the solid cores may be different in different formulations. The size of a solid core defines the surface area of the core. The surface area of the core limits the dose of melatonin that can be loaded onto the core. Larger core sizes can carry larger doses of melatonin, but are not ideal when the pellets are loaded into a liquid or a gummy dosage form. Large pellets may be difficult to swallow or may be destroyed by chewing. Smaller pellets are easier to swallow and are less likely to be chewed.

The active coating is a coating over the solid core and includes melatonin as a therapeutically active ingredient. The source of melatonin is a powder advantageously selected to be substantially pure (such as at least 99.8% pure melatonin), but also have a very small particle size. The melatonin powder is used directly in the dosage form. In a particular example, the melatonin is not dissolved in a solvent prior to being placed in the active coating.

The term "particle size" as used here refers to the size of individual particles making up a powder, which may be polycrystalline. The sizes of individual particles in a powder are not usually uniform; instead they are distributed over a range of sizes, which may vary around a median particle size.

A conventional technique of reporting measurements of particle size to report the D-values D10, D50, and D90 for a powder sample. D10 is the size for which 10% of the sample's mass is particles with a critical dimension less than the value. D50 is the diameter of the particles for which 50% of the sample's mass is smaller than the value and 50% of a sample's mass is larger than the value. D90 is the critical dimension of the particles for which 90% of the sample's mass is smaller than the value and 10% of a sample's mass is larger than the value. A particle size of a powder sample may be measured by sieving, laser diffraction, light scattering, and/or image analysis. The critical dimension refers to one of the dimensions of an individual particle from one side to the other. On a sphere, for example, the critical dimension would be the diameter.

In some examples of the composition, the median particle size of individual melatonin crystals in the powder is in the range of 5 μm to 40 μm. In some examples of the composition, the particle size distribution is D10≤5, D50≤20, and D90≤40.

Using small melatonin particles is advantageous for several reasons. First, because melatonin has low solubility in the intestines, small particles provide large melatonin surface area to enhance the dissolution. Second, the small particles allow melatonin to be dispersed more uniformly across the surface of the solid core.

The active coating also includes a hydrophilic binder that binds the melatonin particles together over the solid core. The active coating may be prepared by blending the melatonin, binder, and water together to form a liquid coating with the melatonin particles dispersed therein. The solid cores may be coated with the active coating using a conventional pellet coating mechanism such as fluid bed coating or the like.

In a particular example, the hydrophilic binder is a hydrogel-forming polymer. A hydrogel-forming polymer is a polymer capable of absorbing water. The hydrogel-forming polymer may act as a release-controlling polymer to provide a sustained release of melatonin into the gastrointestinal tract over a desired time period. Hydrogel forming polymers useful for the binder may include, for example cellulosic polymers such as carboxymethylcelluloses, methylcelluloses, hydroxypropylcelluloses, and hydroxypropylmethylcelluloses; hyaluronates; alginates; polysaccharides, heteropolysaccharides, pectins; poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines, lecithins; miglyols; polylactic acid; polyhydroxybutyric acid; mixtures thereof, copolymers thereof, derivatives thereof, and the like.

Hydroxypropyl methylcellulose is used in certain particular formulations of the dosage form because it forms a hydrogel, is safe, and works well with melatonin.

The active coating may include an acid blended with the hydrophilic binder and melatonin. If used, the acid imparts an acidic pH to the aqueous matrix formed from combining the hydrophilic binder and melatonin with water during processing.

The acid may be a low molecular weight carboxylic acid such as citric acid, succinic acid, tartaric acid, or the like.

The amount of carboxylic acid is sufficient to impart an acidic pH to the hydrogel matrix. Some suitable pH ranges for the hydrogel matrix provided by the amount of carboxylic acid include 0.1 to 5, 1 to 5, 2 to 5, 2 to 4.5, 3 to 5, 3 to 4.5, 3.3 to 5, or 3.4-4.5, or 4.4 or less.

The active coating may be prepared by blending the active coating ingredients together with water. The hydrophilic binder will absorb some of the water, forming an aqueous matrix in which the melatonin particles are dispersed. This aqueous matrix may be applied to the solid core by a pharmaceutical coating technique such as fluid bed coating or the like.

An optional subcoat may be added over the active coating if desired. The subcoat may be selected to serve a particular function.

The subcoat may act as a physical barrier between the active coating and the enteric coating to prevent materials in the active coating and enteric coating from interacting with each other.

The subcoat may act as a release controlling coating that affects the melatonin release kinetics from the pellet. Such a subcoat can be selected to provide a desired release profile in the gastrointestinal tract.

The subcoat may be adapted to provide pH control around the active coating. Because melatonin has a low aqueous solubility above pH=4.4, the subcoat can be used to impart a local pH at or below 4.4 when water from the gastrointestinal tract comes into contact with the subcoat. In such a case, the subcoat material includes a hydrogel-forming polymer and an acid.

When the hydrogel-forming polymer in the subcoat contacts water, it swells as it absorbs the water to form a hydrogel matrix. The hydrogel matrix then creates an aqueous environment around the core. The acid in the hydrogel lowers the pH of the hydrogel to 4.4 or below or from 0.1 to 4.4. The acidic hydrogel may help keep the melatonin within a local acidic environment where the melatonin remains soluble, regardless of the pH of the region of the gastrointestinal tract in which the pellet is located.

Hydrogel forming polymers useful for the subcoat may include, for example cellulosic polymers such as carboxymethylcelluloses, methylcelluloses, hydroxypropylcelluloses, and hydroxypropylmethylcelluloses; hyaluronates; alginates; polysaccharides, heteropolysaccharides, pectins; poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines, lecithins; miglyols; polylactic acid; polyhydroxybutyric acid; mixtures thereof, copolymers thereof, derivatives thereof, and the like.

An separation coating may be placed between the core and subcoat if the subcoat contains the acid. The purpose of the separation coating is to separate the acid in the subcoat from the melatonin in the active coating until after ingestion. Hydrogel forming polymers useful for the separation coat may include, for example cellulosic polymers such as carboxymethylcelluloses, methylcelluloses, hydroxypropylcelluloses, and hydroxypropylmethylcelluloses; hyaluronates; alginates; polysaccharides, heteropolysaccharides, pectins; poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines, lecithins; miglyols; polylactic acid; polyhydroxybutyric acid; mixtures thereof, copolymers thereof, derivatives thereof, and the like. HPMC is used as the separation coating material in a particular example.

The enteric coating may be placed over the individual pellets or over the subcoat or separation coating if present. The enteric coating substantially prevents the melatonin from releasing from the pellet in the stomach. Enteric coating materials have a pH-dependent solubility. In the low pH of the stomach, enteric coating materials are typically substantially insoluble. Because of this, the enteric coating remains intact in the stomach, which substantially prevents melatonin in the pellets from releasing into the stomach.

Enteric coating materials have a dissolution pH above which they become soluble. The dissolution pH is typically a pH found in a person's intestines. Once the pellets enter a region with a pH at or above the dissolution pH, the enteric coating dissolves. As the enteric coating dissolves, melatonin releases from the pellet into the intestines where it can be absorbed systemically by the body.

The enteric coating material may be selected based on its dissolution pH to ensure the melatonin is released from the pellet in the desired region of the gastrointestinal tract. Examples of enteric coating materials include shellac, cellulose acetate phthalate, polyvinyl acetate phthalate, ethyl cellulose/sodium alginate, hypromellose acetate succinate, or a methacrylic acid-based polymer or co-polymer such as methacrylic acid-ethyl acrylate copolymer.

Examples of enteric coatings with their dissolution pHs are reported in Table 1.

TABLE 1

Examples of Enteric Coating Materials

| Brand | Company | Generic Name | Dissolution pH |
|---|---|---|---|
| KOLLICOAT® MAE 30DP | BASF Corp. | Methacrylic acid-ethyl acrylate copolymer | 5.5 and above |
| EUDRAGIT® FS 30D | Evonik Industries AG | Methacrylic copolymer with carboxylic acid functional groups | 7 and above |
| EUDRAGIT® S100 | Evonik Industries AG | Anionic copolymers based on methacrylic acid and methyl methacrylate. | 7 and above |
| AQOAT® AS-HF | Shin Etsu Chemical Co., Ltd | Hypromellose acetate succinate | 6 and above |

The pellets are adapted to be carried to the stomach in the aqueous carrier, disperse in the stomach, and pass through the stomach without substantially releasing melatonin into the stomach. In certain examples, the pellets release the melatonin within the pH range found in the intestines in a sustained release for at least 3 and up to 10 hours. In a particular example, the pellets may release melatonin over a period of 3-10 hours after ingestion regardless of the pH environment it passes through. This sustained release melatonin from the pellets may help the subject remain asleep through the night.

The pellets are administered to treatment subjects as part of an oral pharmaceutical dosage form. In addition to the pellets, the dosage form includes a carrier material. The carrier material is a material in which the pellets are dispersed prior to being ingested.

In order to prevent the enteric coating from dissolving in the carrier material, the carrier material has a pH below the dissolution pH of the enteric coating. The pH may be an inherent quality of the carrier material itself or may be imparted to the carrier material by an acid in the carrier material. The amount of acid in the carrier material is an amount sufficient to impart the desired pH to the carrier material.

The carrier material may have many different forms, but in many examples of the composition, it is an aqueous carrier material. In an aqueous carrier material, water is used as part of the medium.

In certain examples of the composition, the composition is designed to be ingested by drinking, giving the composition a beverage or beverage-like dosage form. In this manner, the pellets are swallowed along with the carrier material when the treatment subject drinks the liquid. This dosage form may be beneficial to subjects who have difficulty swallowing pills. Here, the pellets become entrained with the liquid carrier material and are ingested at the same time.

The liquid carrier material may be made many different ways. In certain examples, the liquid carrier material is composed of water and the acid. It may also include other beverage making ingredients such as, for example, flavors, sweeteners, preservatives, surfactants, emulsifiers, carbonation, viscosity modifiers, and sequestrants among others.

The liquid carrier material form may include an acid such as an acid described above. The acid will create an acidic environment within the dosage form to substantially prevent the enteric coating on the pellets from dissolving in the carrier material or during processing. The amount of acid in the liquid carrier material is sufficient to impart a pH of 0.5 to 5, 1 to 5, 2 to 5, 3 to 5, 3 to 4.5, or 3 to 4 to the liquid carrier material solution.

In certain examples of the composition, the dosage form is a gummy that has the pellets dispersed therein. In such example, the carrier material is suitable for preparing a gummy dosage form.

The gummy carrier material includes a gelling agent that forms the physical structure of the gummy. Examples of gelling agents include, but are not limited to, pectin, gelatin, HPMC, or another conventional gelling agent material.

The gummy carrier material may include an acid. The acid will create an acidic microenvironment within the gummy to substantially prevent the enteric coating on the pellets from dissolving in the gummy or during processing. The amount of acid in the gummy carrier material is sufficient to impart a pH of 0.5 to 5, 1 to 5, 2 to 5, 3 to 5, 3 to 4.5, or 3 to 4 to the gummy dosage form.

The gummy carrier material also includes water, which the gelling agent absorbs, causing it to swell and form the physical structure of the gummy. The amount of water used will depend on the gelling agent selected.

The gummy dosage form may be flavored with a flavoring agent and/or a sweetener. There are many different conventional flavoring agents that may be used. Likewise there are many different natural and artificial sweeteners that may be used.

The carrier material, whether it be liquid, gummy, or otherwise, may include melatonin either in solid form or soluble form therein. By including an amount of melatonin in the carrier material, the carrier material provides an initial burst dose of melatonin to help the subject fall asleep. The remaining melatonin, which is in the pellets then provide a sustained release of melatonin in the intestines to help the subject remain asleep through the night.

The total melatonin dose in a given unit dosage form may be either 100% in the pellets or divided between the pellets and carrier material. In certain examples, the composition has, by % melatonin in the pellet to % melatonin in the carrier material: 50% pellet:50% carrier material; 60% pellet:40% carrier material; 70% pellet:30% carrier material; 80% pellet:20% carrier material; 90% pellet:10% carrier material; 95% pellet:5% carrier material.

The dosage form may be administered orally to a human or animal patient in a therapeutically effective amount, which is an amount that is sufficient to provide a therapeutic benefit affecting a disease or condition in the body.

A therapeutically effective amount of melatonin may be 0.1-1,000 mg/day, including 0.1-25 mg/day, 0.1-10 mg/day, 1-20 mg/day, 1-10 mg/day, 2-10 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective. The weight in mg is often calibrated to the body weight of the patient in kg, thus these example doses may also be written in terms of mg/kg of body weight per day.

In practice, the therapeutically effective amount may vary depending on numerous factors associated with the patient, including age, weight, height, severity of the condition, administration technique, and other factors. The therapeutically effective amount administered to a patient may be determined by medical personnel taking into account the relevant circumstances.

The therapeutically effective amount may be determined or predicted from empirical evidence. Specific dosages may vary according to numerous factors and may be initially determined on the basis of experimentation.

The composition may be administered as a single dose or as part of a dosage regimen. For a dosage regimen, the therapeutically effective amount is an adjustable dose to provide a desired therapeutic response.

Multiple doses may be administered at a predetermined time interval and subsequent doses may be proportionally reduced or increased, depending on the situation.

It should be understood that where this disclosure makes reference to treating a condition, that the terms "treat," "treating," or any other variation of the word "treat" include prevention of, management of, and substantial symptom relief from the condition.

The composition may be prepared by making the pellets and the carrier material separately, then combining them into the final dosage form. If the carrier material is liquid, the pellets may be added directly to the liquid.

If the carrier material is a gummy, the pellets may be combined with the gelling agent prior to gelling and subsequently allowing the gelling process to take place with the pellets therein. This process places the pellets within the gummy so that when the gummy is placed in the mouth and chewed or swallowed the pellets this delivers the pellets to the mouth and gastrointestinal tract.

The pellets may be prepared by obtaining the desired size of solid core and applying the coatings thereto. The active coating may be applied to the solid cores by coating the solid cores with the active coating material. The active coating material may be a solution of melatonin, binder, and water. Coating the solid cores with the active coating may be performed by fluid bed coating or the like. The active coating may be dried over the cores.

The enteric coating may be applied using a conventional enteric coating technique, such as fluid bed coating or the like. The enteric coating may be dried after application.

EXAMPLE

The following example is provided to illustrate aspects of a particular examples of the composition. The scope of possible examples is not limited to the details of this example.

A particular example of the composition is prepared according to the following procedure.

In a Wurster Model 3200 Fluid Bed Coater, 200 kg MCC inert nonpareil spheres (VIVAPUR® Grade 1000 with a diameter of 1 mm to 1.4 mm) are loaded. 10 kg of micronized melatonin dispersed in a 10% aqueous solution of HPMC (PHARMACOAT® 603) is gradually spray coated onto the MCC spheres at an inlet air temperature to 100 degrees F.

After the micronized melatonin has been sprayed onto the nonpareil spheres, 5 g of a 10% aqueous solution of HPMC (PHARMACOAT® 603) is spray coated over the micronized melatonin layer.

50 kg of citric acid dissolved in a 10% aqueous solution of HPMC (PHARMACOAT® 603) is spray coated over the HPMC layer.

An enteric coating suspension with a dry weight of 32 kg is spray coated over the citric acid layer. The enteric coating suspension includes 27.7 kg KOLLICOAT® MAE 30D, 2.8 kg PLASACRYL® T20, and 1.5 kg Triethyl citrate.

After the coated spheres are discharged from the coater, they are screened to remove any agglomerated spheres or fines.

The finished enteric coated spheres are added to HPMC gummies at the start of the gelling/incubation/curing period, with a target of anywhere between 0.05 mgs to 20 mgs of melatonin per gummy. The pH of the gummy matrix is kept below 4.0 with the use of acceptable buffers or acids. Colorants or flavors may be added to the gummy as desired.

This disclosure describes exemplary embodiments, but not all possible embodiments of the compositions and methods. Where a particular feature is disclosed in the context of a particular example, that feature can also be used, to the extent possible, in combination with and/or in the context of other examples. The compositions and methods may be embodied in many different forms and should not be construed as limited to only the examples described here.

The compositions and methods are not limited to the details described in connection with the example embodiments. There are numerous variations and modification of the compositions and methods that may be made without departing from the scope of what is claimed.

That which is claimed is:

1. A composition comprising a therapeutically effective oral pharmaceutical dosage form comprising:

(a) an aqueous carrier material having an acidic pH; and (b) a plurality of individual pellets having a first dose of melatonin therein, the individual pellets comprising (i) a solid core; (ii) an active coating over the solid core, the active coating including melatonin and a hydrophilic binder; and (iii) an enteric coating over the active coating, a dissolution pH of the enteric coating being higher than the acidic pH of the aqueous carrier material, the individual pellets further comprising a separation coating over the active coating, a subcoat between over the separation coating, and enteric coating over the subcoat, wherein the subcoat includes a hydrogel-forming polymer and an acid, the acid imparting a pH of 0.1 to 4.4 to the hydrogel-forming polymer, and the separation coating separates the acid from the melatonin, wherein the dosage form is a beverage or gummy.

2. The composition of claim 1, wherein the melatonin is a powder having a median melatonin particle size of 5 μm to 40 μm.

3. The composition of claim 1, wherein the aqueous carrier material includes a second dose of melatonin therein and dosage form releases the second dose of melatonin into the subject's oral cavity and stomach.

4. The composition of claim 1, wherein the dosage form is a beverage.

5. The composition of claim 1, wherein the dosage form is a gummy and the aqueous carrier material is a gummy gelling agent.

6. The composition of claim 1, wherein the aqueous carrier material is hydroxypropyl methylcellulose, the solid core is a microcrystalline cellulose bead having a diameter of 0.1 to 2 mm, the hydrophilic binder includes hydroxypropyl methylcellulose, the melatonin is a powder having a median melatonin particle size of 5 μm to 40 μm lodged in the hydrophilic binder, the separation coating includes hydroxypropyl methylcellulose, the hydrogel-forming polymer includes hydroxypropyl methylcellulose, the acid includes citric acid, and the separation coating includes hydroxypropyl methylcellulose.

7. A method comprising administering a therapeutically effective amount of an oral pharmaceutical dosage form to a patient in need thereof, the dosage form comprising:

(a) an aqueous carrier material having an acidic pH; and (b) a plurality of individual pellets having a first dose of melatonin therein, the individual pellets comprising (i) a solid core; (ii) an active coating over the solid core, the active coating including melatonin and a hydrophilic binder; and (iii) an enteric coating over the active coating, a dissolution pH of the enteric coating being higher than the acidic pH of the aqueous carrier material, the individual pellets further comprising a separation coating over the active coating, a subcoat between over the separation coating, and enteric coating over the subcoat, wherein the subcoat includes a hydrogel-forming polymer and an acid, the acid imparting a pH of 0.1 to 4.4 to the hydrogel-forming polymer, and the separation coating separates the acid from the melatonin, wherein the dosage form is a beverage or gummy.

8. The method of claim 7, wherein the melatonin is a powder having a median melatonin particle size of 5 μm to 40 μm.

9. The method of claim 7, wherein the aqueous carrier material includes a second dose of melatonin therein and dosage form releases the second dose of melatonin into the subject's oral cavity and stomach.

10. The method of claim 7, wherein the dosage form is a beverage and.

11. The method of claim 7, wherein the dosage form is a gummy and the aqueous carrier material is a gummy gelling agent.

12. The method of claim 7, wherein the aqueous carrier material is hydroxypropyl methylcellulose, the solid core is a microcrystalline cellulose bead having a diameter of 0.1 to 2 mm, the hydrophilic binder includes hydroxypropyl methylcellulose, the melatonin is a powder having a median melatonin particle size of 5 μm to 40 μm lodged in the hydrophilic binder, the separation coating includes hydroxypropyl methylcellulose, the hydrogel-forming polymer includes hydroxypropyl methylcellulose, the acid includes citric acid, and the separation coating includes hydroxypropyl methylcellulose.

13. The method of claim 7, wherein the dosage form is therapeutically effective for assisting the patient to sleep.

14. A method comprising:

combining an aqueous carrier material with a plurality of individual pellets to form a therapeutically effective oral pharmaceutical dosage form;

the aqueous carrier material having an acidic pH; and the a plurality of individual pellets having a first dose of melatonin therein, the individual pellets comprising (i) a solid core; (ii) an active coating over the solid core, the active coating including melatonin and a hydrophilic binder; and (iii) an enteric coating over the active coating, a dissolution pH of the enteric coating being higher than the acidic pH of the aqueous carrier material, the individual pellets further comprising a separation coating over the active coating, a subcoat between over the separation coating, and enteric coating over the subcoat, wherein the subcoat includes a hydrogel-forming polymer and an acid, the acid imparting a pH of 0.1 to 4.4 to the hydrogel-forming polymer, and the separation coating separates the acid from the melatonin, wherein the dosage form is a beverage or gummy.

15. The method of claim 14, wherein the melatonin is a powder having a median melatonin particle size of 5 μm to 40 μm.

16. The method of claim 14, wherein the aqueous carrier material includes a second dose of melatonin therein and dosage form releases the second dose of melatonin into the subject's oral cavity and stomach.

17. The method of claim 14, wherein the dosage form is a gummy and the aqueous carrier material is a gummy gelling agent.

* * * * *